United States Patent
Van Lieshout et al.

(10) Patent No.: US 10,079,086 B2
(45) Date of Patent: Sep. 18, 2018

(54) PROCESSING OF BOUND AND UNBOUND MAGNETIC PARTICLES

(71) Applicant: KONINKLIJKE PHILIPS N.V., Eindhoven (NL)

(72) Inventors: Ron Martinus Laurentius Van Lieshout, Geldrop (NL); Joannes Baptist Adrianus Dionisius Van Zon, Waalre (NL); Toon Hendrik Evers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/409,922

(22) PCT Filed: Jun. 20, 2013

(86) PCT No.: PCT/IB2013/055072
§ 371 (c)(1),
(2) Date: Dec. 19, 2014

(87) PCT Pub. No.: WO2014/001982
PCT Pub. Date: Jan. 3, 2014

(65) Prior Publication Data
US 2015/0187479 A1 Jul. 2, 2015

Related U.S. Application Data

(60) Provisional application No. 61/665,922, filed on Jun. 29, 2012.

(51) Int. Cl.
*H01F 7/20* (2006.01)
*H01F 7/02* (2006.01)
(Continued)

(52) U.S. Cl.
CPC ........... *H01F 7/0294* (2013.01); *G01N 21/55* (2013.01); *G01N 21/552* (2013.01); *H01F 7/206* (2013.01);
(Continued)

(58) Field of Classification Search
CPC ........................................................ H01F 3/12
(Continued)

(56) References Cited

U.S. PATENT DOCUMENTS 3,945,343 A * 3/1976 Berkowitz ............. G03G 19/00
118/623
3,967,892 A * 7/1976 Whited .............. G03G 15/0803
399/270
(Continued)

FOREIGN PATENT DOCUMENTS

EP       2003214 A2    12/2008
WO  2007129275 A2    11/2007
(Continued)

*Primary Examiner* — Alexander Talpalatski (57) ABSTRACT

The invention relates to an apparatus (100) and a method for the processing of magnetic particles (MP) provided in a processing chamber (114) with a binding region (116) to which said magnetic particles (MP) can (specifically) bind. Removal of unbound magnetic particles (MP) from the binding region (116) is achieved by first separating them from the binding region (116) by gravitational forces and then moving them further away by magnetic forces. Gravitational forces can for example be generated by tilting the binding region with a tilting unit (156). The prior separation by gravitational forces prevents that unbound magnetic particles (MP) are captured in a cluster with bound magnetic particles.

16 Claims, 4 Drawing Sheets

(51) Int. Cl.
*G01N 21/552* (2014.01)
*G01N 21/55* (2014.01)

(52) U.S. Cl.
CPC .. *G01N 2201/061* (2013.01); *H01F 2007/208* (2013.01)

(58) Field of Classification Search
USPC .......................................................... 335/284
See application file for complete search history.

(56) References Cited

U.S. PATENT DOCUMENTS

| | | | | |
|---|---|---|---|---|
| 4,361,397 A | * | 11/1982 | Katakura | G03G 21/0047 399/356 |
| 4,457,257 A | * | 7/1984 | Murakami | G03G 15/095 399/264 |
| 4,540,272 A | * | 9/1985 | Abe | G03G 15/0126 399/207 |
| 4,797,335 A | * | 1/1989 | Hiratsuka | G03G 15/0907 399/314 |
| 5,047,807 A | * | 9/1991 | Kalyandurg | G03G 15/09 399/264 |
| 5,184,194 A | * | 2/1993 | Mosehauer | G03G 15/095 399/279 |
| 5,445,971 A | | 8/1995 | Rohr | |
| 5,458,785 A | * | 10/1995 | Howe | B03C 1/035 210/222 |
| 7,326,350 B2 | * | 2/2008 | Mueller | B03C 1/035 210/222 |
| 7,622,046 B2 | * | 11/2009 | Rundt | B03C 1/284 210/222 |
| 8,476,080 B2 | * | 7/2013 | Talmer | B01L 3/5082 436/179 |
| 2004/0235196 A1 | * | 11/2004 | Colin | B03C 1/035 436/526 |
| 2004/0265903 A1 | * | 12/2004 | Mueller | B03C 1/035 435/7.1 |
| 2005/0199503 A1 | | 9/2005 | Woodruff | |
| 2009/0062129 A1 | | 3/2009 | McKernan et al. | |
| 2009/0191553 A1 | | 7/2009 | Hendrickson | |
| 2009/0251136 A1 | * | 10/2009 | Prins | B82Y 25/00 324/228 |
| 2010/0297626 A1 | | 11/2010 | McKernan et al. | |
| 2010/0308945 A1 | * | 12/2010 | Zantl | B01L 3/50273 335/219 |
| 2012/0028342 A1 | | 2/2012 | Ismagilov et al. | |
| 2012/0262565 A1 | * | 10/2012 | Kahlman | G01N 21/552 348/79 |
| 2012/0329039 A1 | * | 12/2012 | Kahlman | B01L 3/5027 435/5 |

FOREIGN PATENT DOCUMENTS

| | | |
|---|---|---|
| WO | 2008115723 A1 | 9/2008 |
| WO | 2009016533 A2 | 2/2009 |
| WO | 2011036634 A1 | 3/2011 |
| WO | 2011073867 A1 | 6/2011 |
| WO | 2011158174 A1 | 12/2011 |

* cited by examiner

PROCESSING OF BOUND AND UNBOUND MAGNETIC PARTICLES

CROSS-REFERENCE TO PRIOR APPLICATIONS

This application is the U.S. National Phase application under 35 U.S.C. § 371 of International Application No. PCT/IB2013/055072, filed on Jun. 20, 2013, which claims the benefit of U.S. Provisional Patent Application No. 61/665,922, filed on Jun. 29, 2012. These applications are hereby incorporated by reference herein.

FIELD OF THE INVENTION

The invention relates to a method and an apparatus for the processing of magnetic particles that can bind to a binding region.

BACKGROUND OF THE INVENTION

The WO 2010/134005 A1 discloses an optical biosensor in which frustrated total internal reflection (FTIR) of a light beam is detected and evaluated with respect to the amount of magnetic particles at a binding region. Magnetic fields are used to attract the magnetic particles to said surface for an accelerated binding and to wash unbound magnetic particles away before a detection is made.

SUMMARY OF THE INVENTION

It is an object of the invention to provide means that allow for the processing of magnetic particles at a binding region with improved accuracy.

This object is achieved by an apparatus according to claim 1, a method according to claim 2, and a use according to claim 15. Preferred embodiments are disclosed in the dependent claims.

According to a first aspect, the invention relates to an apparatus for the processing of magnetic particles which comprises the following components:

A chamber that is called "processing chamber" in the following and that comprises a binding region to which magnetic particles can bind. Additionally or alternatively, the apparatus may comprise an accommodation space in which such a reaction chamber can be accommodated. The reaction chamber may then for example be a part of an exchangeable cartridge.

A magnetic field generator for generating a magnetic field in the processing chamber. The magnetic field generator may for example comprise one or more permanent magnets and/or electromagnets.

At tilting unit for controllably changing the inclination of the binding region, i.e. its orientation with respect to the direction of gravity.

The "processing" that can be done with the described apparatus may comprise any kind of e.g. physical or chemical manipulation. In particular, the "processing" may include a detection procedure with which magnetic particles or target components bound thereto are qualitatively or quantitatively detected.

The term "magnetic particles" shall comprise both permanently magnetic particles as well as magnetizable particles, for example superparamagnetic beads. The size of the magnetic particles typically ranges between 3 nm and 50 µm. Moreover, the magnetic particles may comprise bound target components one is actually interested in. The magnetic particles are usually provided to the processing chamber in some carrier or medium, for example a sample fluid.

The "processing chamber" is typically an empty cavity or a cavity filled with some substance like a gel that may absorb a sample substance; it may be an open cavity, a closed cavity, or a cavity connected to other cavities by fluid connection channels.

The "binding region" may extend over the whole surface of the processing chamber, though it will typically be only a part thereof (e.g. lying in the surface of one wall of the processing chamber). The interaction of magnetic particles to the binding region may be of any type, most preferably an intermolecular binding. Moreover, the binding is preferably "specific" in that only particular ones of the magnetic particles present in the processing chamber are able to bind to the binding region. The magnetic particles may for example be provided with capture sites for target components of a sample fluid, wherein only magnetic particles with captured target components are able to bind to the binding region. In this case, bound magnetic particles are an indicator for the presence of the target components of interest.

The invention further relates to a method for the processing of magnetic particles. Said method may particularly be executed with an apparatus of the kind described above, and it comprises the following steps:

a) Providing magnetic particles in a processing chamber that has a binding region.

b) Letting magnetic particles bind on the binding region.

c) Separating unbound magnetic particles, which have not bound to the binding region in the previous step, from the binding region by gravitational forces.

d) Generating with a magnetic field generator a magnetic field which moves the aforementioned magnetic particles that have been separated from the binding region further away from the binding region (i.e. their distance to the binding region is further increased).

Step b) of letting the magnetic particles bind to the binding region is usually a passive step, requiring mainly that the magnetic particles are given sufficient time to migrate to the binding region and to bind thereto (e.g. driven by chemical affinity). Optionally, this step b) may be actively assisted, for example by attracting magnetic particles magnetically to the binding region in order to accelerate the migration process.

The separation of unbound magnetic particles in step c) shall particularly comprise that the distance between magnetic particles and the binding region is increased for magnetic particles that are initially close to or even in contact to the binding region. Moreover, the gravitational force is preferably the only (or at least the dominating) external force acting on the magnetic particles during this step. It may for example amount to more than 50%, preferably more than 90% of the mean external forces acting on a magnetic particle during the separation step c). Other external forces (of minor influence) which may act on the magnetic particles are hydrodynamic forces (conveyed by the flow of the surrounding medium) and magnetic forces (which are preferably minimized during this step). It should be noted that thermal forces (conveyed by thermal motion of surrounding particles) are considered in this context as "internal forces" and not included in the comparison with gravitational forces.

The gravitational forces used in the separation step c) may have their origin in earth's gravity. Pulling unbound magnetic particles away from the binding region may then be achieved by tilting the binding region, i.e. by giving it an inclination other than horizontal. As an extreme case, the binding region may be turned upside down such that the (unbound) magnetic particles are below the binding region.

Another example of gravitational forces are forces of inertia, particularly centrifugal forces that may for example be generated by rotating the binding region.

The apparatus and the method are both based on the inventive concept that unbound magnetic particles are separated from the binding region first by gravitational forces. Explanations and definitions provided for the apparatus are therefore valid for the method, too, and vice versa.

The apparatus and the method according to the invention allow for an improved accuracy of procedures carried out with magnetic particles bound to a binding region. This is because unbound magnetic particles, which could disturb such a procedure, are first separated from the binding region very efficiently by gravitational forces (and then optionally further separated by magnetic forces). The prior use of gravitational forces has the advantage that unbound magnetic particles do not adhere to bound magnetic particles, as is often the case if only magnetic forces are used for the separation. In the latter case, unbound magnetic particles may form clusters (chains) with bound magnetic particles which prevents their separation from the binding region.

In the following, various preferred embodiments of the invention will be described that relate to the apparatus as well as to the method described above.

The apparatus may preferably comprise a control unit which is designed for coordinating the inclination of the binding region with the generation of the magnetic field(s). This coordination may preferably take place according to the method defined above. In particular, the binding region may be inclined (deviating from horizontal) for a time sufficient to remove unbound magnetic particles from it by a predetermined distance, and thereafter a magnetic field may be generated that continues the separation of the magnetic particles from the binding region. The control unit may for example be realized in dedicated electronic hardware and/or digital data processing hardware with associated software.

In a preferred embodiment of the invention, the binding region can assume a horizontal orientation below the magnetic particles, i.e. at the bottom of the processing chamber. The horizontal orientation may particularly be assumed during the phase in which magnetic particles bind to the binding region. In this embodiment, gravity tends to move magnetic particles from the interior of the processing chamber towards the binding region (at the binding region itself, the effect of the gravitational forces is counterbalanced by the contact force to the binding region).

In another preferred embodiment, the binding region can assume a horizontal orientation above the magnetic particles, i.e. at the top of the processing chamber. In this case a separation of unbound magnetic particles from the binding region by gravitational forces occurs naturally without a need for tilting the binding region. The magnetic particles can reach the binding region (for binding thereto) for example due to Brownian motion and/or with the help of magnetic attraction.

The apparatus may be a one-piece element in which all components are permanently attached to each other. Tilting of the binding region will in this case usually comprise the tilting of the whole apparatus. In a preferred embodiment, the processing chamber with the binding region is located in an exchangeable cartridge which can be introduced into some processing device, wherein cartridge and processing device together constitute an apparatus according to the invention. Such a processing device (without cartridge) is therefore also considered to fall under the scope of the present invention. The cartridge will typically be a disposable component that is used only once for the processing of a medium at hand, for example a sample fluid like blood, saliva, or urine.

In a further preferred embodiment of the invention, the binding region can be tilted with respect to the magnetic field generator (and/or with respect to other components of the apparatus). This embodiment is particularly possible if the binding region is located in a separate cartridge because tilting of the binding region can then be achieved by tilting (only) said cartridge.

The time during which gravitational forces act on unbound magnetic particles (at the binding region) is preferably sufficient to move said particles a distance away from bound magnetic particles that is larger than about two times the (mean) diameter of the magnetic particles, preferably larger than three or larger than five times said diameter. Investigations show that unbound magnetic particles which are at least these distances away from bound ones do not form clusters or chains with bound magnetic particles (and hence do not return to the binding region) when the magnetic field is applied that shall move unbound magnetic particles further away from the binding region.

According to another embodiment of the invention, a further magnetic field (called "intermediate magnetic field" in the following) is generated before the separation of unbound magnetic particles from the binding region by gravitational forces. This "intermediate magnetic field" is intended to induce the formation of chains of magnetic particles, and it is therefore applied only for a comparable short duration that suffices to achieve this (e.g. a few seconds). The chains of magnetic particles, which persist for some time after the intermediate magnetic field has been switched off, are able to move faster through the surrounding medium during the action of gravitational forces. In order to assist this effect, the magnetic field lines of the intermediate magnetic field are preferably oriented parallel to the (later) gravitational forces (i.e. usually vertical).

Preferably, the unbound magnetic particles are (or can be) moved to a location outside the binding region, particularly a region where they do not affect the processing at the binding region and in the adjacent volume of the processing chamber. This movement may be achieved by an appropriate magnetic field (acting after the gravitational forces). The location outside the binding region may be such that the part of the processing chamber above the binding region is (approximately) free of unbound magnetic particles, thus allowing for example the transmission of light through this volume without disturbances by unbound magnetic particles.

In a preferred embodiment of the invention, the magnetic field generator comprises a horse-shoe magnet with (at least) two poles that are located at the binding region, i.e. at a position sufficiently close to the binding region to allow for the generation of magnetic fields at said region and in the adjacent volume of the processing chamber.

Preferably, at least one of aforementioned poles of the horse-shoe magnet can be activated separately. When the poles of the horse-shoe magnet are arranged symmetrically with respect to the binding region (or the processing chamber), activation of a single pole will usually generate a magnetic field that is asymmetric with respect to the binding region. Such a field can for example be used to move (unbound) magnetic particles to a location outside the binding region.

In a further embodiment of the invention, the magnetic field generator comprises (additionally or alternatively)

magnets that are disposed on opposite sides of the binding region (and hence usually also on opposite sides of the processing chamber). Activating these magnets separately in an appropriate manner can be used to pull unbound magnetic particles away from the binding region.

The processing of the magnetic particles in the processing chamber may particularly include a processing by optical means. To this end, the apparatus may comprise a light source for illuminating the binding region. The illumination may for example be direct, particularly through the processing chamber and the medium therein. To avoid disturbances of the illumination of the binding region in this case, it is usually important that the medium traversed by the illumination is free of (unbound) magnetic particles. The illumination of the binding region may also be achieved by evanescent waves, generated for example by total internal reflection of an illuminating light beam emitted by the light source.

The apparatus may optionally comprise a light detector for detecting light coming from the binding region. This light may for example be the aforementioned totally internally reflected light of the light source, wherein a reduction in intensity is an indication of bound magnetic particles at the binding region. This approach is known as "frustrated total internal reflection" (FTIR) and described in more detail in the WO 2008/155716 A1, WO 2009/016533A2, or WO 2008/072156 A2. In another example, the detected light may be light of fluorescence that is stimulated in the binding region.

The invention further relates to the use of the apparatus described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

Platforms for the specific detection of marker molecules in bodily fluids are for example provided by the Magnotech® technology developed by the applicant. An example of a marker molecule is troponin-I (cTnI) for the detection of cardio-vascular disease. The detection technique is based on immuno-assays in combination with the optical detection of superparamagnetic nanoparticles (beads) on the surface of a cartridge. Many platforms use Total Internal Reflection (TIR) illumination by creating an evanescent optical field near the surface. This technique is surface sensitive and in principle free of interference from the nanoparticles in the bulk.

Figure 1:
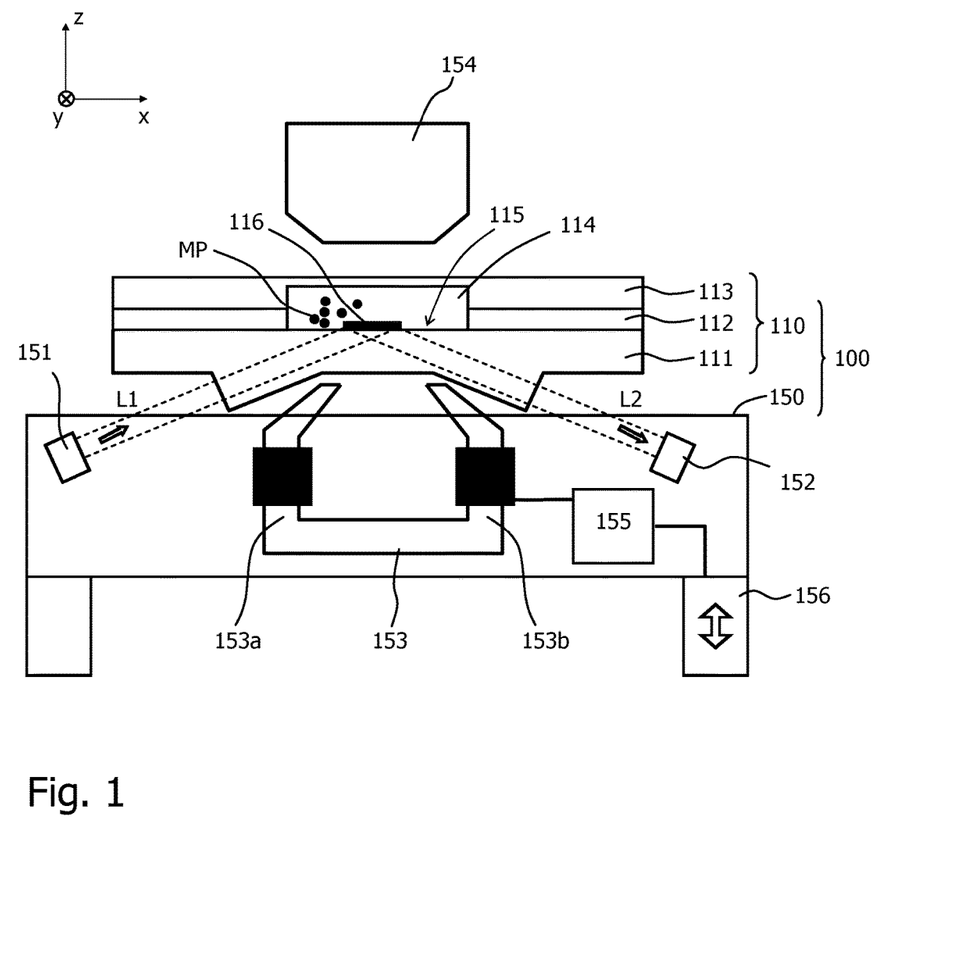
FIG. 1 schematically shows a side view of an apparatus according to the present invention comprising an FTIR detection at the binding region.

FIG. 1 schematically shows a section through a first embodiment of a (sensor) apparatus 100 that applies the aforementioned technology and is further designed according to the present invention. The apparatus 100 comprises (a) a reader 150 with an accommodation space for an exchangeable cartridge 110 and (b) said cartridge 110.

The apparatus 100 is used for the detection of target components comprised in a sample fluid (e.g. blood) that fills a processing chamber 114 of the cartridge. The cartridge 110 is composed of a transparent base part 111 which borders the processing chamber 114 at its bottom side and which provides a processing surface 115. The side walls of the processing chamber 114 are constituted by an intermediate layer 112, for example a tape into which openings for the processing chamber and associated fluidic channels (not shown) have been cut. The processing chamber 114 is covered at its top side by a (e.g. plastic) cover 113.

At least one binding region 116 is located on the processing surface 115. It comprises capture probes, for example antibodies, to which certain substances can specifically bind. These substances may particularly be magnetic particles MP with probes (antibodies) on their surface that have (specifically) captured target components of interest from the sample medium in the processing chamber 114.

FIG. 1 further shows a magnetic field generator, here comprising a horse-shoe magnet 153 (with two poles 153a, 153b) below the binding region 116 and a top magnet 154 above it. The poles of these magnets may individually be controlled by a control unit 155 of the reader 150 for generating a magnetic field B in the processing chamber 114 by which the magnetic particles MP can be manipulated.

FIG. 1 further indicates a light source 151 for emitting an input light beam L1 into the cartridge 110. This input light beam is totally internally reflected at the binding region 116 and then leaves the cartridge 110 as an output light beam L2 towards a light detector 152. These light beams can be used to detect target components of the sample fluid that are specifically bound to magnetic particles MP and the capture probes of the binding region 116. Further details of this assay and the optical detection of target components by frustrated total internal reflection (FTIR) may be found for example in the WO 2008/115723 A1, which is incorporated into the present text by reference.

In order to create a fast reaction, the amount of probes (antibodies) to capture the target molecules (e.g. a cardiac marker) needs to be high and as a consequence the amount of magnetic particles in the bulk needs to be high. This causes several problems:

(a) Due to incorrect alignment of the cartridge and scattering at impurities in the cartridge material itself (e.g. tiny air bubbles, scratches), a fraction of the incoming light may be scattered into the volume of the cartridge instead of being confined near the surface. This causes bulk illumination. Because of scattering at the large amount of magnetic particles in the bulk (the 'bead cloud'), also light from the bulk is therefore detected. This raises the background level and decreases the contrast of the image. Due to the non-uniform distribution of the bead cloud, the background will also be non-uniform.

(b) The evanescent illumination field decays exponentially with the distance to the surface. Typically the decay length is of the order of 100 nm. The exponential decay causes the intensity of the magnetic particles on the surface to be very sensitive to the height above the surface. Although the height-dependent intensity can give useful information (e.g. about the bond length), it also causes that only a fraction of the magnetic particles on the surface can be detected. By using bright-field illumination from the top of the cartridge as an additional means instead of TIR illumination, the height dependence can be eliminated. However due to the large amount of free nanoparticles, the bright-field illumination is hampered.

(c) During the magnetic washing (i.e. a magnetic field removes unbound particles from the surface), vertical clusters of magnetic particles are attached to bound magnetic particles. Information about the length of these vertical clusters can improve the performance of the detection. However due to the short decay length of the evanescent field, the size of these vertical clusters is not visible. By using bright field illumination (e.g. in combination with a varying focus depth of the objective lens), an estimate of the vertical cluster size can be obtained. However due to the large amount of free magnetic particles, the bright-field illumination is hampered.

In order to address the above problems, it is proposed to remove the unbound beads (magnetic particles) after or possibly during the reaction from the processing chamber. Due to the nature of the superparamagnetic beads they will form chains when an external magnetic field is applied. This can hamper the removal of all the unbound magnetic beads from the field of view because a fraction of them will be magnetically coupled to the bound beads on the binding region. One solution is to still remove the large excess of beads leaving only a small part still bound to the surface bound beads. When applying a magnetic field perpendicular to the surface the beads will form chains in the same orientation allowing an easy detection.

The cartridge also can be tilted or even turned upside down to allow sedimentation of the unbound beads from the functionalized surface. When thereafter the magnetic fields are applied the unbound beads will form only chains with other unbound beads, thus removing all the unbound beads from the beads bound to the surface. This will be explained in more detail in the following.

Experiments have shown that the binding process in a setup which has been put upside down can be done equally well when the actuation protocol is slightly adapted. The advantage of using the setup upside down is that the gravitational force can improve the washing process.

Figure 2:
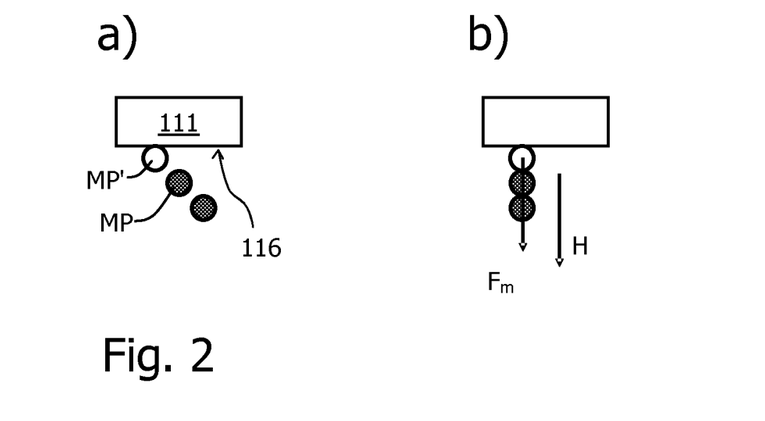
FIG. 2 illustrates the effect of a magnetic field acting on bound and unbound magnetic particles at an overhead binding region when gravitational forces act only for a short time.

This is illustrated in FIG. 2a), which sketches the situation directly after the binding process. Bound magnetic particles MP' and free magnetic particles MP are present in close proximity because the binding process uses a magnetic force to keep all the particles near the binding region 116.

In FIG. 2b), a magnetic washing field H is switched on to move the free particles away from the surface. However, actually magnetic clustering occurs: due to the magnetic interactions between the magnetic particles, a large number of free beads will couple magnetically to the particles bound to the surface. Therefore these free beads cannot be removed. The presence of these free beads near the bound beads distorts the (optical) signal of the bound beads (e.g. the intensity of the bound bead is altered).

Figure 3:
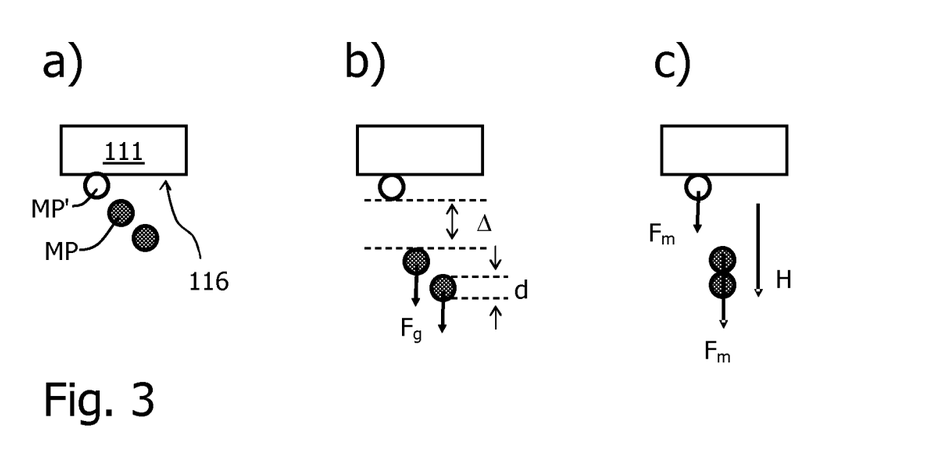
FIG. 3 shows the situation of FIG. 2 when gravitational forces act for a longer time.

FIG. 3 illustrates how this problem can be solved by shortly using a gravitational force. FIG. 3a) corresponds to the starting situation of FIG. 2a).

According to FIG. 3b), gravitational force $F_g$ is used directly after the binding process to move the free magnetic particles MP away from the bound magnetic particles MP' of the binding region 116 without having an interaction force between them.

Once the free magnetic particles have moved some distance $\Delta$ from the bound particles (typically a distance of 5-10 µm is sufficient), the magnetic washing force $F_m$ can be used to move the free beads further away from the surface. This is shown in FIG. 3c).

Because the distance $\Delta$ between the bound beads and the free beads is large enough, the magnetic interaction becomes negligible (the magnetic interaction force $F_m$ decreases with the 4th power of the distance between the particles). The surface contains only bound particles without free particles attached to them. The (optical) signal is then a better representation for the number of bound beads on the surface.

Typically one needs approximately a distance $\Delta$ between the bound and the free beads of approximately 5 times the bead diameter d, i.e. $\Delta \geq 5$ d. Then the magnetic attraction force between the beads is low enough to prevent magnetic coupling.

Some numerical examples are as follows:

For beads with a diameter of d=500 nm, sedimentation velocity is about 100 nm/s. The distance $\Delta$ to travel is then 5·500 nm=2500 nm. The time the gravitational force has to work is therefore 2500 nm/(100 nm/s)=25 s.

For d=1000 nm beads, a velocity of 400 nm/s, the distance to travel is $\Delta$=5000 nm, with a required time of 5000/400 s=12.5 s.

So the time frame depends on the bead diameter and of course the density of the bead (in the above calculation a typical density of 1.8 g/cm$^3$ was used).

When using gravity to remove unbound magnetic beads from the binding region, an improvement may be achieved by first switching on an intermediate magnetic field shortly. This will form chains of magnetic beads, particularly of unbound beads to bound beads. Then the gravitational force is allowed to do its work. Due to the (vertical) alignment of the chains and the hydrodynamic coupling between them, they will 'fall' faster than isolated magnetic beads. Finally the magnetic field is switched on again to attract the beads away from the binding region.

Figure 4:
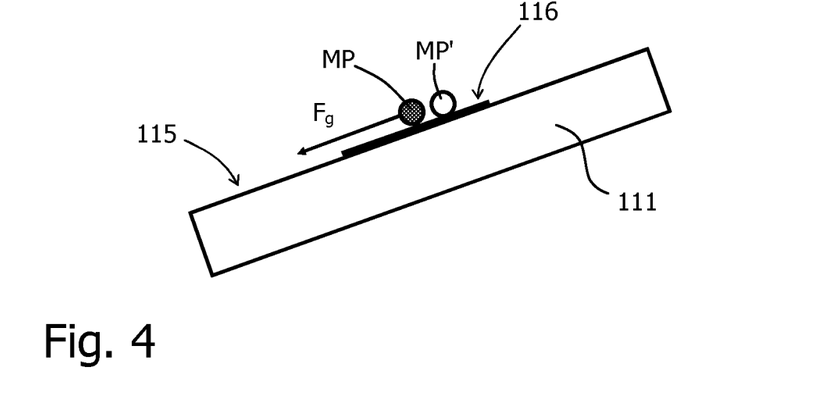
FIG. 4 illustrates the effect of gravitational forces on magnetic particles at an inclined binding region.

With the setup in the normal position, i.e. the processing surface 115 and the binding region 116 being oriented horizontally below the processing chamber 114, the gravitational force can also be used to remove free, unbound magnetic particles from the printed spot (binding region 116) by means of a sideways translation. This is illustrated in FIG. 4. By tilting the surface 115, a component of the gravitational force $F_g$ directed along the surface will become available. This force component will move free particles MP away from the bound particles MP' in the spot. Similar to FIG. 2 a magnetic force cannot achieve this effect because the magnetic interactions between bound and free particles which will keep the free beads near the bound beads in the spot. This effect is more pronounced when the number of bound beads in the spot is larger.

In the apparatus 100 of FIG. 1, the above principles can be realized with the help of a "tilting unit" 156 that is indicated in the Figure as one foot of the apparatus 100 which can be varied in height, controlled by the control unit 155. Accordingly, the whole apparatus 100 with the binding region 115 can be tilted with respect to gravity (z-direction).

Figure 5:
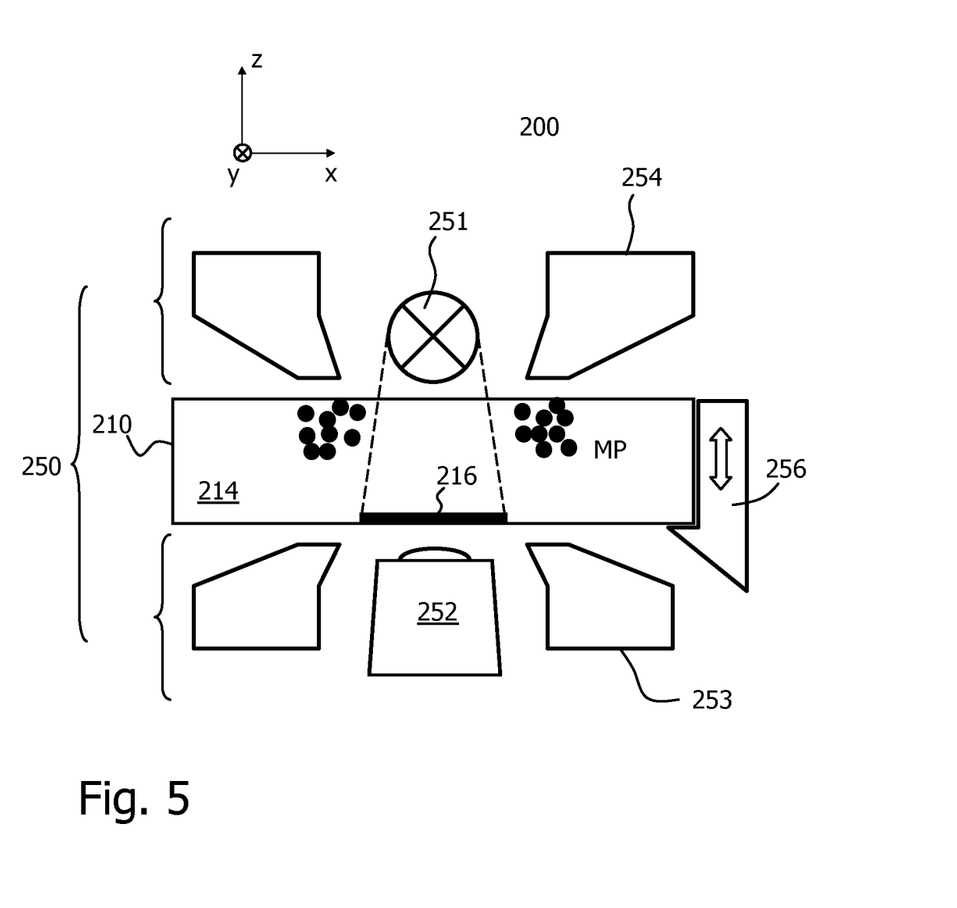
FIG. 5 schematically shows a side view of an apparatus according to the present invention comprising a bright-field illumination of the binding region.

FIG. 5 schematically shows a side view of a sensor apparatus 200 according to a second embodiment of the present invention. The sensor apparatus 200 comprises a reader 250 and an exchangeable cartridge 210. The cartridge 210 has a processing chamber 214, filled with a fluid comprising magnetic particles MP, and a binding region 216. Moreover, a tilting unit 256 is symbolically indicated with which the cartridge 210 can controllably be tilted with respect to the reader 250.

The reader 250 comprises a bottom magnet 253 and a top magnet 254 ("washing magnet"), which now both are horse-shoe magnets. This configuration offers the opportunity for a light source 251 directly above the binding region 216 while moving the magnetic beads MP away from the light path. Thus a bright field illumination of the binding region 216 is achieved which can be used with a high NA objective lens 252 directly below the binding zone (cf. WO 2011/036634A1).

In summary, the above approach is characterized by the following features:

1. Having the binding region with the antibodies in an orientation such that gravity directs particles substantially away from the region.

2. "Applying gravity" (no magnetic force) for a sufficiently long time for the magnetic particles to travel more than several bead diameters d from the region.

3. Applying a magnetic force directing the particles substantially away from the detection area (defined as the area where the particles still interfere with the detected signal, e.g. by scattering).

Removal of unbound magnetic particles can additionally or alternatively be done by the available electromagnets, using the top magnet 154 (washing magnet) in combination with one of the pole tips 153a, 153b of the bottom magnet (horse-shoe magnet 153) to create an off-center magnetic field direction pulling the beads from the processing chamber 114. It is also possible to bring the beads back to the reaction area by either using only the top magnet or by the combination of both the bottom and top magnet.

Accordingly, the present invention relates to a method to remove unbound beads from a processing chamber having one or more of the following features:

Unbound beads are removed from a processing chamber by means of magnetic forces.

Unbound beads are removed from a processing chamber by creating a magnetic field trap that is outside the field of view by using one of the pole tips of the horse-shoe magnet.

The contrast of the image is enhanced by removing unbound beads.

A bright field illumination is enabled by removing unbound beads.

A bright field illumination is enabled by partially removing unbound beads, i.e. by creating chains of the (limited) amount of unbound beads linked to the bound beads on the surface.

The (partial) removal of unbound beads is enabled by using gravitation force (e.g. in a configuration where top and bottom magnet are reversed).

Figure 6:
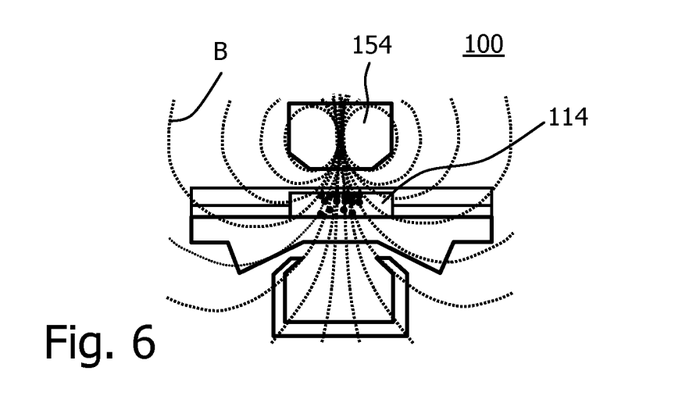
FIG. 6 illustrates the apparatus of FIG. 1 when the magnetic field is generated by the top magnet only.
Figure 7:
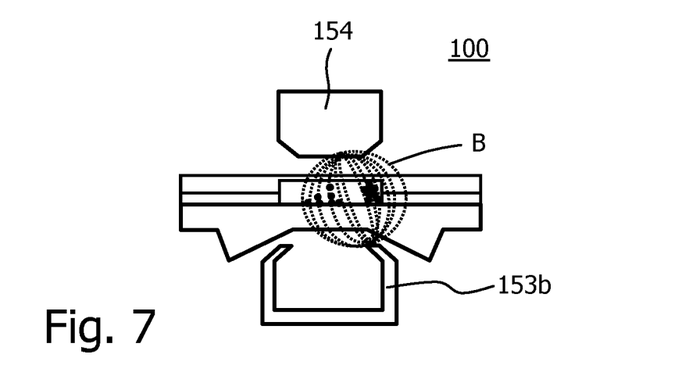
FIG. 7 illustrates the apparatus of FIG. 1 when the magnetic field is generated by the top magnet and one pole of the bottom horse-shoe magnet.
Figure 8:
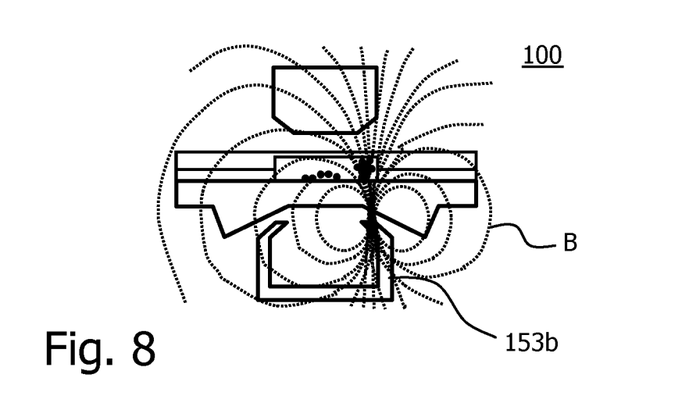
FIG. 8 illustrates the apparatus of FIG. 1 when the magnetic field is generated by one pole of the bottom horse-shoe magnet only.

FIGS. 6-8 illustrate a preferred procedure of generating and applying magnetic fields in the processing chamber 114 to achieve some of the above objectives. This procedure starts after the usual magnetic actuation (designed to have the optimal specific binding of superparamagnetic beads to the surface) and an optional intermediate step of particles separation by gravitational forces.

According to FIG. 6, the unbound beads are pulled away from the field of view by first pulling them to the top of the processing chamber 114 by the top (wash) magnet 154, which removes them from the processing surface but not from the bulk above the surface.

According to FIG. 7, the beads can then be moved to the side of the processing chamber by using both the top magnet 154 and one of the pole tips 153b of the horse-shoe magnet. In addition the use of the top magnet may force the small amount of free beads to form chains on top of the already bound beads making them invisible for detection.

According to FIG. 8, the beads can then be pulled to the side of the chamber, by using only one of the pole tips 153b of the horse-shoe magnet. Only due to the creation of magnetic fields that are almost parallel to the surface the unbound beads will form chains with the bound beads that are also in parallel to the surface hampering the detection.

Optionally, one can alternate between one of the pole tips of the horse-shoe magnet 153 and the top magnet 154 to ensure that the beads are removed from the field of view.

In summary, the invention relates to an apparatus and a method for the processing of magnetic particles provided in a processing chamber with a binding region to which said magnetic particles can (specifically) bind. Removal of unbound magnetic particles from the binding region is achieved by first separating them from the binding region by gravitational forces and then moving them further away by magnetic forces. Gravitational forces can for example be generated by tilting the binding region with a tilting unit.

The basic idea behind using the gravitational force is to prevent the magnetic attachment of free beads to the bound beads on the surface. Generally when the washing magnet is switched on, bound and free beads are magnetized and the free beads will magnetically couple to the bound beads. The gravitational force allows the free beads to move away from the bound beads and thus prevents that unbound magnetic particles are captured in a cluster with bound magnetic particles.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for processing of magnetic particles (MP, MP), the method comprising:

providing magnetic particles (MP, MP') in a processing chamber comprising a binding region;

letting magnetic particles (MP') bind to the binding region;

separating unbound magnetic particles (MP) from the binding region by gravitational forces ($F_g$) comprising controllably changing an inclination of the binding region; and generating with a magnetic field generator a magnetic field (H) which moves said separated unbound magnetic particles (MP) further away from the binding region.

2. An apparatus for processing magnetic particles (MP, MP'), the apparatus comprising:

a processing chamber with a binding region to which magnetic particles (MP') can bind;

a magnetic field generator for generating a magnetic field (H) in the processing chamber; and a tilting unit for controllably changing an inclination of the binding region, wherein a light detector is provided for detecting light (L2) coming from the binding region.

3. The apparatus according to claim 2, wherein the binding region is configured to assume a horizontal orientation below or above magnetic particles (MP, MP') present in the processing chamber, while magnetic particles (MP') bind to the binding region.

4. The apparatus according to claim 2, wherein the processing chamber with the binding region is located in an exchangeable cartridge.

5. The apparatus according to claim 2, wherein the binding region is configured to be tilted with respect to the magnetic field generator.

6. The method according to claim 1, wherein the gravitational forces ($F_g$) act for a time that is sufficient to move unbound magnetic particles (MP) a distance ($\Delta$) of more than about two times their diameter (d) away from magnetic particles (MP') bound to the binding region.

7. The method according to claim 1, wherein an intermediate magnetic field is generated prior to the separating of the unbound magnetic particles (MP) from the binding region.

8. The method according to claim 1, wherein the unbound magnetic particles (MP) can be moved to a location outside the binding region.

9. The method according to claim 1, wherein the magnetic field generator comprises a horse-shoe magnet having poles located at the binding region.

10. The apparatus according to claim 2, wherein the magnetic field generator comprises a horse-shoe magnet comprising poles located at the binding region, and at least one pole of the horse-shoe magnet is configured to be activated separately.

11. The apparatus according to claim 2, wherein the magnetic field generator comprises magnets disposed on opposite sides of the binding region.

12. The apparatus according to claim 2, wherein a light source is provided for illuminating the binding region.

13. The apparatus according to claim 2, further comprising:

a control unit configured to coordinate the inclination of the binding region and the generating of the magnetic field (H).

14. The apparatus according to claim 2, wherein the apparatus is configured to perform molecular diagnostics, biological sample analysis, chemical sample analysis, food analysis, and/or forensic analysis.

15. The apparatus according to claim 2, wherein a light source is provided for emitting an input light beam (L1) into the binding region, the input light beam being totally internally reflected at the binding region and leaving the binding region as the light (L2) detected by the light detector.

16. The apparatus according to claim 4, further comprising:

an accommodation space configured to receive the exchangeable cartridge.

* * * * *